United States Patent [19]
Dean

[11] Patent Number: 5,993,775
[45] Date of Patent: *Nov. 30, 1999

[54] RADIOACTIVELY LABELED PEPTIDES COMPRISING A SINGLE THIOL MOIETY

[75] Inventor: Richard T. Dean, Bedford, N.H.

[73] Assignee: Diatide, Inc., Londonderry, N.H.

[ * ] Notice: This patent is subject to a terminal disclaimer.

[21] Appl. No.: 09/162,195

[22] Filed: Sep. 28, 1998

Related U.S. Application Data

[62] Continuation-in-part of application No. 08/244,336, filed as application No. PCT/US92/10716, Nov. 19, 1992, Pat. No. 5,866,097, which is a continuation-in-part of application No. 07/807,062, Nov. 27, 1991, Pat. No. 5,443,815, which is a continuation-in-part of application No. 08/471,741, Jun. 6, 1995, Pat. No. 5,814,297, which is a division of application No. 07/807,062, Nov. 27, 1991, Pat. No. 5,443,815, which is a continuation-in-part of application No. 08/564,315, filed as application No. PCT/US94/05895, May 25, 1994, which is a continuation-in-part of application No. 08/073,577, Jun. 7, 1993, Pat. No. 5,561,220.

[51] Int. Cl.$^6$ .......................... A61K 51/00; A61M 36/14
[52] U.S. Cl. ...................... 424/1.69; 424/1.11; 424/1.65; 530/300; 530/326; 534/10; 534/14
[58] Field of Search ................... 424/1.11, 1.65, 424/1.69, 9.1; 534/10–16; 530/300, 326–331; 206/223, 569, 570

[56] References Cited

U.S. PATENT DOCUMENTS

| | | |
|---|---|---|
| 4,986,979 | 1/1991 | Morgan . |
| 5,443,815 | 8/1995 | Dean . |
| 5,561,220 | 10/1996 | Dean . |
| 5,670,133 | 9/1997 | Zamora . |
| 5,736,122 | 4/1998 | Dean et al. ............... 424/1.69 |
| 5,807,537 | 9/1998 | Dean . |
| 5,814,297 | 9/1998 | Dean et al. ............... 424/1.69 |
| 5,866,097 | 2/1999 | Dean et al. ............... 424/1.69 |
| 5,879,658 | 3/1999 | Dean et al. ............... 424/1.69 |

FOREIGN PATENT DOCUMENTS

WO 90/15818  12/1990  WIPO .

OTHER PUBLICATIONS

Deutsch, et al, (1986) "The Chemistry of Rhenium and Technetium as Related to the Use of Isotopes of these Elements in Therapeutic and Diagnostic Nuclear Medicine," Nucl. Med. Biol., 13, 465–477.

*Primary Examiner*—S. Mark Clardy
*Assistant Examiner*—Dameron Jones
*Attorney, Agent, or Firm*—Patricia A. McDaniels

[57] ABSTRACT

The invention relates to radiolabeled imaging of a mammalian body. The invention in particular provides for reagents labeled with technetium-99m for such imaging. The invention provides peptides which bind technetium-99m, rhenium-186, or rhenium-188 and which can be targeted to specific sites within a mammalian body.

21 Claims, No Drawings

RADIOACTIVELY LABELED PEPTIDES COMPRISING A SINGLE THIOL MOIETY

This application is a continuation-in-part of U.S. patent application Ser. No. 08/244,336, filed Oct. 28, 1994, and now U.S. Pat. No. 5,866,097 which is a 371 of PCT/US92/10716, filed Nov. 19, 1992 and is a continuation-in-part of U.S. patent application Ser. No. 07/807,062, filed Nov. 27, 1991 now U.S. Pat. No. 5,443,815; this application is also a continuation-in-part of U.S. patent application Ser. No. 08/471,741, filed Jun. 6, 1995, and now U.S. Pat. No. 5,814,297 which is a divisional of U.S. patent application Ser. No. 07/807,062, filed Nov. 27, 1991 now U.S. Pat. No. 5,443,815; this application is also a continuation-in-part of U.S. patent application Ser. No. 08/564,315, filed Oct. 4, 1996, which is a 371 of PCT/US94/05895, filed May 25, 1994 and a continuation-in-part of U.S. patent application Ser. No. 08/073,577, filed Jun. 7, 1993 now U.S. Pat. No. 5,561,220.

This invention relates to peptides for use in diagnostic imaging, and methods for producing labeled peptides. Specifically, the invention relates to technetium-99m, rhenium-186, and rhenium-188 labeled peptides, methods and kits for making such peptides, and methods for using such peptides.

BACKGROUND OF THE INVENTION

A variety of radionuclides are known to be useful for radioimaging, including $^{67}$Ga, $^{99m}$Tc (technetium-99m), $^{111}$In, $^{123}$I, $^{125}$I, $^{169}$Yb or $^{186}$Re. The use of chelating agents for radiolabeling large polypeptides such as proteins is known in the prior art. Methods for labeling peptides and polypeptides with technetium-99m have been disclosed in the prior art.

Byrne et al., U.S. Pat. No. 4,434,151 describe homocysteine thiolactone bifunctional chelating agents that can couple radionuclides to terminal amino-containing compounds capable of localizing in an organ or tissue to be imaged.

Fritzberg, U.S. Pat. No. 4,444,690 describes a series of technetium-chelating agents based on 2,3-bis(mercaptoacetamido)propanoate.

Gansow et al., U.S. Pat. No. 4,472,509 teach methods of manufacturing and purifying metal chelate-conjugated monoclonal antibodies.

Byrne et al., U.S. Pat. Nos. 4,571,430 and 4,575,556 describe novel homocysteine thiolactone bifunctional chelating agents for chelating radionuclides that can couple radionuclides to terminal amino-containing compounds capable of localizing in an organ or tissue to be imaged.

Nicolotti et al., U.S. Pat. No. 4,861,869 describe bifunctional coupling agents useful in forming conjugates with biological molecules such as antibodies. This reference describes compounds such as S-benzoylmercaptoacetylglycylglycylglycine.

European Patent Application No. 84109831.2 describes technetium chelating complexes of bisamido-bisthiol-ligands and salts thereof, used primarily as renal function monitoring agents.

European Patent Application No. 86100360.6 describes dithiol, diamino, or diamidocarboxylic acids or amine complexes useful for making technetium imaging agents.

European Patent Application No. 88104755.9 describes various S-protected mercaptoacetylglycylglycine chelating groups bound to large proteins such as antibodies.

Albert et al., UK Patent Application No. 8927255.3 disclose radioimaging using somatostatin derivatives such as octreotide labeled with $^{111}$In via a chelating group bound to the amino terminus.

Flanagan et al., European Patent Application No. 90306428.5 disclose technetium-99m labeling synthetic peptide fragments via a set of organic chelating molecules.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Davison et al., Inorg. Chem. 20: 1629–1632 (1981) disclose oxotechnetium chelate complexes.

Fritzberg et al., J. Nucl. Med. 23: 592–598 (1982) disclose a technetium chelating agent based on N,N'-bis(mercaptoacetyl)-2,3-diaminopropanoate.

Byrne and Tolman, J. Nucl. Med. 24: P126 (1983) disclose a bifunctional thiolactone chelating agent for coupling technetium-99m to biological molecules.

Bryson et al., Inorg. Chem. 27: 2154–2161 (1988) describe thiolate ligands for complexing with technetium.

Bryson et al., Inorg. Chem. 29: 2948–2951 (1990) describe thiolate ligands for complexing with technetium.

Kwekkeboom et al., J. Nucl. Med. 32: 981 (1991) Abstract #305 relates to radiolabeling somatostatin analogues with $^{111}$In.

Albert et al., Abstract LM10, 12th American Peptide Symposium (1991) describe uses for $^{111}$In-labeled diethylenetriaminopentaacetic acid-derivatized somatostatin analogues.

Dean, co-pending U.S. patent application Ser. No. 07/653,012, now abandoned, teaches reagents and methods for preparing peptides comprising a technetium-99m chelating group having the general structure Cp(aa)Cp, wherein Cp is a protected cysteine and (aa) is an amino acid, the chelating group being covalently linked to a specific binding peptide for radioimaging in vivo, and is hereby incorporated by reference.

Reno and Bottino, European Patent Application No. 87300426.1 disclose radiolabeling antibodies with technetium-99m.

Bremer et al., EPC Application No. 87118142.6 disclose organ-specific radioimaging using technetium-99m radiolabeled proteins.

Pak et al., European Patent Application No. WO 88/07382 disclose a method for labeling antibodies with technetium-99m.

Goedemans et al., PCT Application No. WO 89/07456 describe radiolabeling proteins using cyclic thiol compounds, particularly on 2-iminothiolane and derivatives.

Schochat et al., PCT Application No. WO 89/09405 disclose direct radiolabeling of proteins comprised of at least one "pendent" sulfhydryl group.

Dean et al., PCT Application No. WO 89/12625 describe bifunctional coupling agents for technetium-99m labeling of proteins or peptides.

Thornback et al., EPC Application No. 90402206.8 describe preparation and use of radiolabeled proteins or peptides using thiol-containing compounds, particularly 2-iminothiolane.

Stuttle, PCT Application No. WO 90/15818 describes technetium-99m labeling of RGD-containing oligopeptides.

Rhodes, Sem. Nucl. Med. 4: 281–293 (1974) teaches the labeling of human serum albumin with technetium-99m.

Khaw et al., J. Nucl. Med. 23: 1011–1019 (1982) disclose methods for labeling biologically active macromolecules with technetium-99m.

Knight et al., Abstract #209, 37th Annual Meeting, Society for Nuclear Medicine (1990) describe thrombus imaging with technetium-99m labeled peptides.

Cox et al., Abstract, 7th International Symposium on Radiopharmacology, p. 16, 1991, disclose the use of $^{131}$I- and $^{111}$In-labeled somatostatin analogues in radiolocalization of endocrine tumors in vivo by scintigraphy.

SUMMARY OF THE INVENTION

The present invention provides scintigraphic imaging and therapeutic agents that are radioactively-labeled peptides. The peptides of the invention comprise between 7 and 100 amino acid residues, including a radioisotope complexing group covalently linked to a targeting peptide, wherein the complexing group is capable of binding to a radioisotope. The sensitivity of imaging methods using radioactively-labeled peptides is much higher than other techniques known in the art, since the specific binding of the radioactive peptide concentrates the radioactive signal over the cells of interest, for example, tumor cells.

In one embodiment, the present invention provides peptides comprising between 7 and 100 amino acid residues, said peptides including a targeting amino acid sequence covalently linked to a technetium or rhenium complexing sequence through less than twenty amino acids, wherein the complexing sequence comprises a single thiol moiety having a structure:

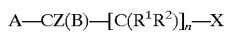

wherein A is H, HOOC, $H_2$NOC, (peptide)-NHOC, (peptide)-OOC or $R^4$; B is H, SH or —NHR$^3$, —N(R$^3$)-(peptide) or $R^4$ Z is H or methyl; X is SH or —NHR$^3$, —N(R$^3$)-(peptide) or $R^4$; $R^1$, $R^2$, $R^3$ and $R^4$ are independently H or straight chain lower alkyl, branched chain lower alkyl, or cyclic lower alkyl; n is 0, 1 or 2; peptide represents the remaining components of the complexing sequence; and: where B is —NHR$^3$ or —N(R$^3$)-(peptide), X is SH and n is 1 or 2; where X is —NHR$^3$ or —N(R$^3$)-(peptide), B is SH and n is 1 or 2; where B is H or $R^4$, A is HOOC, $H_2$NOC, (peptide)-NHOC, (peptide)-OOC, X is SH and n is 0 or 1; where A is H or $R^4$, then where B is SH, X is —NHR$^3$ or —N(R$^3$)-(peptide) and where X is SH, B is —NHR$^3$ or —N(R$^3$)-(peptide); where X is H or $R^4$, A is HOOC, $H_2$NOC, (peptide)-NHOC, (peptide)-OOC and B is SH; and where Z is methyl, X is methyl, A is HOOC, $H_2$NOC, (peptide)-NHOC, (peptide)-OOC and B is SH and n is 0.

The invention also encompasses methods for making the peptides described above; technetium-99m, rhenium-186, and rhenium-188 complexes of such peptides; and methods for using these complexes to image or treat target sites within a mammalian body.

DETAILED DESCRIPTION OF THE INVENTION

The present invention provides peptides that comprise between 7 and 100 amino acid residues, said peptides being useful for imaging or treating target sites within a mammalian body when labeled with a radioisotope. The peptides of the invention include a targeting sequence of amino acids covalently linked to a radioisotope complexing group, wherein the complexing group is capable of binding a radioisotope, preferably technetium-99m, rhenium-186, or rhenium-188. The complexing group preferably consists of additional amino acids or amino acid analogs and thus for the purposes of the present invention is defined as a radioisotope complexing sequence. Preferably, three additional amino acids or amino acid analogs are required to effect complexation of oxotechnetium or oxorhenium. More preferably, two additional amino acids or amino acid analogs are required to effect complexation of oxotechnetium or oxorhenium. The targeting sequence of the peptide is linked to the radioisotope complexing sequence through a limited number of amino acids. Preferably the targeting sequence is linked to the radioisotope complexing sequence through less than twenty amino acids; more preferably, through less than 15 amino acids; most preferably, through less than 10 amino acids.

Labeling with technetium-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo—$^{99m}$Tc generator. Other radionuclides known in the prior art have effective half-lives which are much longer (for example, $^{111}$In, which has a half-life of 67.4 h) or are toxic (for example, $^{125}$I). Both rhenium-186 and rhenium-188 are β-emitters and thus are suitable for therapeutic applications. Rhenium-186 additionally emits a γ-ray at essentially the same energy as the γ emission of technetium-99m, allowing monitoring of biodistribution using the same instrumentation as is used for technetium-99m imaging. Rhenium-188 is available as a no carrier added isotope from a $^{188}$W/$^{188}$Re generator analogous to the $^{99}$Mo—$^{99m}$Tc generator. Those of skill will recognize that the chemical properties of technetium and rhenium are similar or substantially the same, as described in Deutsch, et al. (1986) Nucl. Med. Biol. 13, 465–477.

Peptides of the present invention can be chemically synthesized in vitro. Peptides of the present invention can generally advantageously be prepared on an amino acid synthesizer. The peptides of this invention can be synthesized wherein the complexing amino acid sequence is covalently linked to the targeting peptide during chemical in vitro synthesis, using techniques well known to those with skill in the art. Such peptides are advantageous because specific sites of covalent linkage between the targeting amino acid sequence and the radiolabel complexing amino acid sequence can be controlled. The peptides of the invention are comprised of between 4 and 100 amino acid residues, and are covalently linked to a radioisotope complexing group wherein the complexing group binds a radioisotope. In preferred embodiments, the peptides are covalently linked to radioisotope complexing groups comprising a single thiol moiety having the structure set forth above.

The invention encompasses peptides for labeling with Tc-99m and imaging target sites within a mammalian body comprising between 4 and 100 amino acid residues, covalently linked to a radioisotope complexing group wherein the complexing group binds a radioisotope. The invention encompasses methods for making such peptides covalently linked to a radioisotope complexing group. The invention also includes Tc-99m complexes and methods for preparation of such Tc-99m complexes and methods for using the Tc-99m complexes to image target sites within a mammalian body.

In forming a complex of radioactive technetium or rhenium with the peptides of this invention, the technetium or rhenium complex, preferably a salt of technetium-99m pertechnetate, rhenium-186 perrhenate, or rhenium-188 perrhenate, is reacted with the peptides of this invention in the presence of a reducing agent; in a preferred embodiment, the reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of the peptides of the invention that are to be labeled and a sufficient amount of reducing agent to label the peptide with technetium-99m, rhenium-186, or rhenium-188. Alternatively, the complex may be formed by reacting the peptides of this invention with a pre-formed labile complex of technetium or rhenium and another compound known as a transfer ligand. This process is known as ligand exchange and is well known to those skilled in the art. The labile complex may be formed using such transfer ligands as tartrate, citrate, gluconate or mannitol, for example. Among the technetium-99m pertechnetate, rhenium-186 perrhenate, or rhenium-188 perrhenate salts useful with the present invention are included the alkali metal salts such as the sodium salt, or ammonium salts or lower alkyl ammonium salts. The reaction of the peptides of this invention with technetium pertechnetate or rhenium perrhenate or pre-formed technetium-99m, rhenium-186, or rhenium-188 labile complex can be carried out in an aqueous medium at room temperature. The anionic complex which has a charge of [−1] is formed in the aqueous medium in the form of a salt with a suitable cation such as sodium cation, ammonium cation, mono, di- or tri-lower alkyl amine cation, etc. Any conventional salt of the anionic complex with a pharmaceutically acceptable cation can be used in accordance with this invention.

In another embodiment of the present invention, the peptides of the invention are reduced prior to labeling by incubation with a reducing agent. In a preferred embodiment, the reducing agent is stannous chloride. In an additional preferred embodiment, the reducing agent is a solid-phase reducing agent. The pre-reduced peptide is then labeled by reaction with technetium-99m, rhenium-186, or rhenium-188 under reducing conditions or with pre-reduced technetium-99m, rhenium-186, or rhenium-188 or a technetium-99m, rhenium-186, or rhenium-188 complex.

In a preferred embodiment of the invention, a kit for preparing technetium- or rhenium-labeled peptides is provided. An appropriate amount of the peptide of the invention is introduced into a vial containing a reducing agent, such as stannous chloride or a solid-phase reducing agent, in an amount sufficient to label the peptide with technetium-99m, rhenium-186, or rhenium-188. An appropriate amount of a transfer ligand as described (such as tartrate, citrate, gluconate or mannitol, for example) can also be included. Technetium- or rhenium-labeled peptides of the present invention can be prepared by the addition of an appropriate amount of technetium-99m, rhenium-186, or rhenium-188 or technetium-99m, rhenium-186, or rhenium-188 complex into the vials and reaction under conditions described in Example 2 hereinbelow.

Radioactively labeled peptides provided by the present invention are provided having a suitable amount of radioactivity. In forming the technetium-99m, rhenium-186, or rhenium-188 radioactive anionic complexes, it is generally preferred to form radioactive complexes in solutions containing radioactivity at concentrations of from about 0.01 millicurie (mCi) to 100 mCi per ml.

Technetium-labeled peptides provided by the present invention can be used for visualizing organs such as the kidney for diagnosing disorders in these organs, and tumors, such as gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged. The peptides of the invention are also used to image disease states such as thromboses, atherosclerosis, and the like. The site imaged by the peptides of the invention will be determined by the binding specificity of the targeting amino acid sequence. Rhenium-186 or rhenium-188 labeled peptides of the invention may be used particularly for treatment of tumors bearing the site targeted by the targeting sequence of the peptide of the invention.

In accordance with this invention, the technetium- or rhenium-labeled peptides or anionic complexes either as a complex or as a salt with a pharmaceutically acceptable cation are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 ml to about 10 ml. After intravenous administration, imaging of the organ or tumor in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The labeled peptides and complexes provided by the invention may be administered intravenously in any pharmaceutically acceptable carrier, e.g., conventional medium such as an aqueous saline medium, or in blood plasma medium, as a pharmaceutical composition for intravenous injection. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with 2-(1H-benzo-triazol-1-yl)-1,1,3,3-tetramethyluronium hexafluorophosphate/hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 2

A General Method for Radiolabeling with Technetium-99m 0.1 mg of a peptide prepared as in Example 1 was dissolved in 0.1 ml of 0.05M potassium phosphate buffer (pH 7.4). Technetium-99m gluceptate was prepared by reconstituting a Glucoscan vial (E.I. DuPont de Nemours, Inc.) with 1.0 ml of technetium-99m sodium pertechnetate containing up to 200 mCi and allowed to stand for 15 minutes at room temperature. 25 μl of technetium-99m gluceptate was then added to the peptide and the reaction allowed to proceed at room temperature for 30 min and then filtered through a 0.2 μm filter.

The technetium-99m labeled peptide purity was determined by HPLC using a Vydak 218TP54 analytical column (RP-18, 5 micron, 220×4.6 mm) and eluted with the following gradient: 100% A (0.1%, TFA in $H_2O$) to 100% B ($CH_3CN:H_2O:TFA$, 70:30:0.1) over 10 minutes at a flow rate of 1.2 ml/min; and then held at the 100% B solution for 5 minutes. Radioactive components were detected by an in-line radiometric detector linked to an integrating recorder. Technetium-99m gluceptate and technetium-99m sodium pertechnetate elute between 1 and 4 minutes under these conditions, whereas the technetium-99m labeled peptide eluted after a much greater amount of time.

The following Table illustrates successful technetium-99m labeling of peptides prepared according to Example 1 using the method described herein.

TABLE I

| Peptides Prepared and Radiolabeled | FABMS MH+ Found/Theoretical | Radiochemical Yield | HPLC Rt (min) |
|---|---|---|---|
| YRALVDTLKFVTQAEGAKC.$NH_2$ | 2113/2113.1 | 92% | 11–15.5 |
| GRGDGGC | 769/768.3 | 98% | 13–15 |
| maGGGRGDF[a] | 739/739.3 | 98% | 13–15 |
| PenGGGRALVDTLK—$NH_2$[b] | 1216.3/1216.7 | 98% | 14.8 |
| maGGGGRALVDTLK—$NH_2$ | 1160/1160.5 | 97% | 14.3 |
| mmpGGGRALVDTLK—$NH_2$[c] | 1187.4/1186.7 | 98% | 14.9–15.5 |

[a]ma = mercaptoacetic acid
[b]Pen = L-penicillamine
[c]mmp = 2-mercapto-2-methylpropionic acid It should be understood that the foregoing disclosure emphasizes certain specific embodiments of the invention and that all modifications or alternatives equivalent thereto are within the spirit and scope of the invention as set forth in the appended claims.

---

What is claimed is:

1. A peptide comprising between 7 and 100 amino acid residues, said peptide including a targeting amino acid sequence covalently linked to a technetium or rhenium complexing sequence through less than twenty amino acids, wherein the complexing sequence comprises a single thiol moiety having a structure:

$$A\text{—}CZ(B)\text{—}[C(R^1R^2)]_n\text{—}X$$

wherein

A is H, HOOC, $H_2NOC$, (peptide)-NHOC, (peptide)-OOC or $R^4$;

B is H, SH or $-NHR^3$, $-N(R^3)$-(peptide) or $R^4$;

Z is H or methyl;

X is SH or $-NHR^3$, $-N(R^3)$-(peptide) or $R^4$;

$R^1$, $R^2$, $R^3$ and $R^4$ are independently H, straight chain lower alkyl, branched chain lower alkyl, or cyclic lower alkyl;

n is 0, 1 or 2;

peptide represents the remaining components of the complexing sequence;

and wherein where B is $-NHR^3$ or $-N(R^3)$-(peptide), X is SH and n is 1 or 2;

where X is $-NHR^3$ or $-N(R^3)$-(peptide), B is SH and n is 1 or 2;

where B is H or $R^4$, A is HOOC, $H_2NOC$, (peptide)-NHOC, (peptide)-OOC, X is SH and n is 0 or 1;

where A is H or $R^4$, then where B is SH, X is —$NHR^3$ or —$N(R^3)$-(peptide) and where X is SH, B is —$NHR^3$ or —$N(R^3)$-(peptide);

where X is H or $R^4$, A is HOOC, $H_2NOC$, (peptide)-NHOC, (peptide)-OOC and B is SH;

where Z is methyl, X is methyl, A is HOOC, $H_2NOC$, (peptide)-NHOC, (peptide)-OOC and B is SH and n is 0.

2. The peptide of claim 1, wherein the targeting sequence and the complexing sequence are linked through less than 15 amino acids.

3. The peptide of claim 1, wherein the targeting sequence and the complexing sequence are linked through less than 10 amino acids.

4. A pharmaceutical composition comprising the peptide of claim 1 and a pharmaceutically acceptable carrier.

5. A pharmaceutical composition comprising the peptide of claim 2 and a pharmaceutically acceptable carrier.

6. A pharmaceutical composition comprising the peptide of claim 3 and a pharmaceutically acceptable carrier.

7. The pharmaceutical composition of claim 4, further comprising technetium-99m.

8. The pharmaceutical composition of claim 5, further comprising technetium-99m.

9. The pharmaceutical composition of claim 6, further comprising technetium-99m.

10. The pharmaceutical composition of claim 4, further comprising rhenium-186 or rhenium-188.

11. The pharmaceutical composition of claim 5, further comprising rhenium-$^{186}$ or rhenium-188.

12. The pharmaceutical composition of claim 6, further comprising rhenium-186 or rhenium-188.

13. A kit comprising a sealed vial containing a predetermined amount of the peptide of claim 1 and a sufficient amount of a reducing agent to label the peptide with technetium-99m, rhenium-186, or rhenium-188.

14. A kit comprising a sealed vial containing a predetermined amount of the peptide of claim 2 and a sufficient amount of a reducing agent to label the peptide with technetium-99m, rhenium-186, or rhenium-188.

15. A kit comprising a sealed vial containing a predetermined amount of the peptide of claim 3 and a sufficient amount of a reducing agent to label the peptide with technetium-99m, rhenium-186, or rhenium-188.

16. A technetium-99m complex of the peptide of claim 1.

17. A technetium-99m complex of the peptide of claim 2.

18. A technetium-99m complex of the peptide of claim 3.

19. A rhenium-186 or rhenium-188 complex of the peptide of claim 1.

20. A rhenium-186 or rhenium-188 complex of the peptide of claim 2.

21. A rhenium-186 or rhenium-188 complex of the peptide of claim 3.

* * * * *

SEQUENCE LISTING

<160> NUMBER OF SEQ ID NOS: 6

<210> SEQ ID NO 1
<211> LENGTH: 19
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 1

Tyr Arg Ala Leu Val Asp Thr Leu Lys Phe Val Thr Gln Ala Glu Gly
 1               5                  10                  15
Ala Lys Cys

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence:synthetic
      peptide

<400> SEQUENCE: 2

Gly Arg Gly Asp Gly Gly Cys
 1               5

<210> SEQ ID NO 3
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: residue x is mercaptoacetic acid -continued

```
<220> FEATURE:
<223> OTHER INFORMATION: Description of Artificial Sequence:synthetic
      peptide

<400> SEQUENCE: 3

Xaa Gly Gly Gly Arg Gly Asp Phe
 1               5

<210> SEQ ID NO 4
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: residue x is penicillamine
<220> FEATURE:
<223> OTHER INFORMATION: Description of Artificial Sequence:synthetic
      peptide

<400> SEQUENCE: 4

Xaa Gly Gly Gly Arg Ala Leu Val Asp Thr Leu Lys
 1               5                  10

<210> SEQ ID NO 5
<211> LENGTH: 13
<212> TYPE: PRT
<213> ORGANISM: Artificial Sequence
<220> FEATURE:
<221> NAME/KEY: MOD_RES
<222> LOCATION: (1)
<223> OTHER INFORMATION: residue x is mercaptoacetic acid
<220> FEATURE:
<223> OTHER INFORMATION: Description of Artificial Sequence:synthetic
      peptide

<400> SEQUENCE: 5

Xaa Gly Gly Gly Gly Arg Ala Leu Val Asp Thr Leu Lys
 1               5                  10

<210> SEQ ID NO 6
<211> LENGTH: 12
<212> TYPE: PRT
<213> ORGANISM: Artificial Sequence
<220> FEATURE:
<221> NAME/KEY: MOD_RES
<222> LOCATION: (1)
<223> OTHER INFORMATION: residue x is 2-mercapto-2-methylpropionic acid
<220> FEATURE:
<223> OTHER INFORMATION: Description of Artificial Sequence:synthetic
      peptide

<400> SEQUENCE: 6

Xaa Gly Gly Gly Arg Ala Leu Val Asp Thr Leu Lys
 1               5                  10
```